(12) United States Patent
Fernandez

(10) Patent No.: US 8,788,290 B2
(45) Date of Patent: *Jul. 22, 2014

(54) REMOTE DATA MANAGEMENT SYSTEM WITH BUSINESS INTELLIGENCE IN REAL-TIME

(75) Inventor: Ronald E. Fernandez, Ann Arbor, MI (US)

(73) Assignee: Unival, Inc., Ann Arbor, MI (US)

( * ) Notice: Subject to any disclaimer, the term of this patent is extended or adjusted under 35 U.S.C. 154(b) by 3 days.

This patent is subject to a terminal disclaimer.

(21) Appl. No.: 13/339,447

(22) Filed: Dec. 29, 2011

(65) Prior Publication Data
US 2013/0006665 A1 Jan. 3, 2013

Related U.S. Application Data

(60) Provisional application No. 61/427,989, filed on Dec. 29, 2010.

(51) Int. Cl.
*G06Q 10/00* (2012.01)
*G06Q 50/00* (2012.01)

(52) U.S. Cl.
USPC .................. 705/3; 705/2; 707/600; 707/769; 707/809

(58) Field of Classification Search
CPC ...... G06Q 50/22; G06Q 50/24; G06F 19/322; G06F 19/3487; G06F 17/30592; G06F 17/30563
USPC ............................ 705/2, 3; 707/600, 769, 809
See application file for complete search history.

(56) References Cited

U.S. PATENT DOCUMENTS

| | | | |
|---|---|---|---|
| 7,519,622 B2 | 4/2009 | Fernandez | |
| 2005/0278270 A1* | 12/2005 | Carr et al. | 706/25 |
| 2006/0106787 A1* | 5/2006 | Fernandez | 707/4 |
| 2007/0239666 A1* | 10/2007 | Garcia | 707/2 |
| 2008/0046292 A1* | 2/2008 | Myers et al. | 705/3 |
| 2008/0052113 A1* | 2/2008 | Cauley et al. | 705/2 |
| 2008/0133300 A1* | 6/2008 | Jalinous | 705/7 |
| 2009/0024414 A1* | 1/2009 | Mansour et al. | 705/3 |
| 2009/0254572 A1* | 10/2009 | Redlich et al. | 707/10 |
| 2010/0088117 A1* | 4/2010 | Belden et al. | 705/3 |
| 2010/0228559 A1* | 9/2010 | Boone | 705/1.1 |
| 2010/0274756 A1* | 10/2010 | Inokuchi et al. | 707/602 |
| 2011/0202556 A1 | 8/2011 | Fernandez | |

* cited by examiner

*Primary Examiner* — John Pauls
*Assistant Examiner* — Jonathan Durant
(74) *Attorney, Agent, or Firm* — Brinks Gilson & Lione

(57) ABSTRACT

The present disclosure provides a dynamic data management system and a method of using said system to locate, obtain, analyze, and report desired patient information in real-time. The data management system generally comprises an order in the form of a query that requests information regarding a specific patient or group of patients that resides on an electronics records server; a data collection and conversion system (DCCS), and a business intelligence engine in communication with the DCCS. The DCCS is capable of transporting the information from the electronic records server and creating a document that includes XML data, while the business intelligence engine is capable of breaking down the XML data to form at least one de-normalized fact table that can be used to report the desired information in real-time.

14 Claims, 2 Drawing Sheets

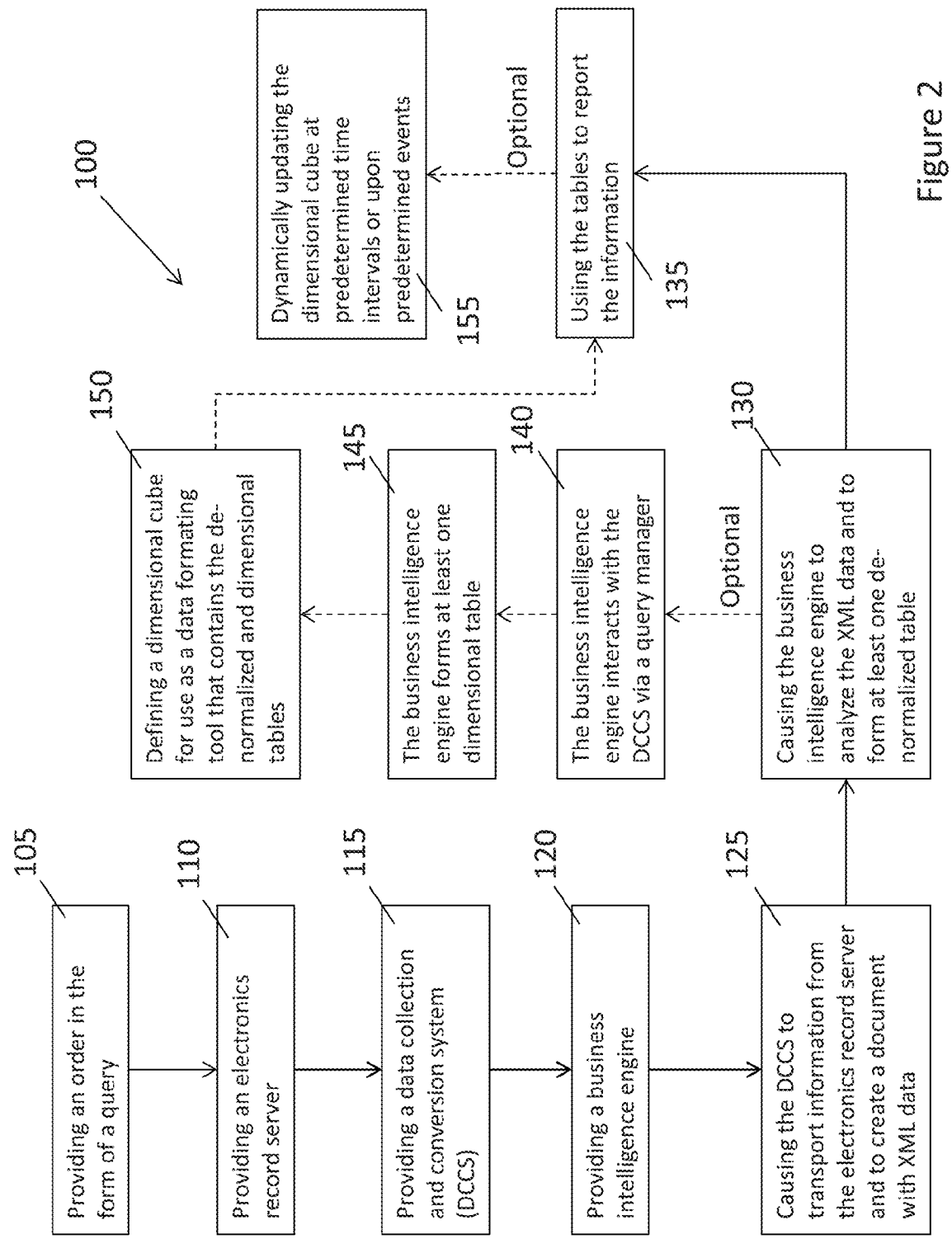

REMOTE DATA MANAGEMENT SYSTEM WITH BUSINESS INTELLIGENCE IN REAL-TIME

CROSS REFERENCE TO RELATED APPLICATION

This application claims priority to U.S. Provisional application No. 61/427,989 filed Dec. 29, 2010, entitled "Remote Data Management System with Business Intelligence in Real-Time," the entire contents of which are herein incorporated by reference.

FIELD

This disclosure relates generally to the field of data collection, and more specifically to a dynamic system and method for collecting data in real-time from disperse data sources, analyzing said data, and reporting the same.

BACKGROUND

Specific information relevant to the health of a patient may be stored in files, records, and other data sources located in many different medical facilities such as physician offices, hospitals, skilled nursing facilities, medical laboratories, free standing radiology clinics and other health care providers. Patient information is often required by organizations that are authorized to receive such information, such as medical service provider plans, governmental agencies, including Medicare and Medicaid, and other authorized organizations. The specific information may be found in many locations, on various media, in numerous formats and amid a considerable amount of non-relevant data. For example, data collection may take the form of extracting data from electronic or paper files and records or collecting data visually by inspection during an on-site audit of a medical facility. Selecting, collecting, abstracting, and organizing the relevant data into a format that is readily analyzed and managed by the resources of a medical service provider plan or other authorized organization is a complex and time consuming task. Thus, authorized organizations have a need and a continual desire for new efficient systems and methods for selecting, collecting, abstracting, organizing, and managing specific medical information from the files of their participating medical and healthcare service providers.

SUMMARY

The present disclosure provides a dynamic data management system and a method of using said system to locate, obtain, analyze, and report desired patient information in real-time. The data management system generally comprises an order in the form of a query that requests information regarding a specific patient or group of patients that resides on an electronics records server; a data collection and conversion system (DCCS), and a business intelligence engine in communication with the DCCS. The DCCS comprises a query processor and an application interface that is capable of linking the query processor with the electronic records server through a generic interface. The query processor may comprise a communication processor, a datastream processor, and an extensible markup language (XML) creation procedure system. The DCCS is capable of transporting the information from the electronic records server and creating a document that includes XML data. The business intelligence engine is capable of breaking down the XML data to form at least one de-normalized fact table that can be used to report the desired information in real-time.

According to another aspect of the present disclosure, the DCCS may comprise a communication channel; a query transmitter; and an XML receiver. The business intelligence engine may also comprise a query manager capable of interacting with the DCCS; and a dynamic extracting, transforming, & loading (ETL) system. The dynamic ETL system may include both dimensional tables and the de-normalized fact tables. The de-normalized tables and dimensional tables define a dimensional cube that is used as a data formatting tool for reporting. The dimensional cube may be dynamically updated at predetermined time intervals or upon predetermined events.

According to another aspect of the present disclosure, the data management system may further comprise a document management and storage system (DMSS) that has an application processor and a tool processor designed to manage and control the storage of electronic documents. The electronic records server may contain one selected from the group of electronic medical records (EMR) and electronic health records (EHR).

According to another aspect of the present disclosure, a method of locating, obtaining, analyzing, and reporting desired patient information in real-time is provided. This method generally comprises the steps of: providing an order in the form of a query that requests information regarding a specific patient or group of patients; providing an electronics records server upon which the information regarding the specific patient or group of patients resides as source information; providing a data collection and conversion system (DCCS) as previously described above and further defined herein; providing a business intelligence engine that is in communication with the DCCS; causing the DCCS to transport the information from the electronic records server and to create a document that includes XML data; causing the business intelligence engine to break down the XML data to form at least one de-normalized fact table containing the desired patient information; and using the de-normalized fact table to report the desired information in real-time.

According to another aspect of the present disclosure, the step of providing a business intelligence engine in communication with the DCCS may further include the use of a business intelligence engine that has a query manager capable of interacting with the DCCS and a dynamic ETL system. The business intelligence engine further forms at least one dimensional table in addition to the at least one de-normalized table. These tables are used to define a dimensional cube for use as a data formatting tool in reporting. The dimensional cube may be dynamically updated when necessary or desired at predetermined time intervals or upon predetermined events.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

FIG. 2 is a schematic representation of a method of locating, obtaining, analyzing, and reporting desired patient information in real-time using the dynamic data management system of FIG. 1.

DETAILED DESCRIPTION

Figure 1:
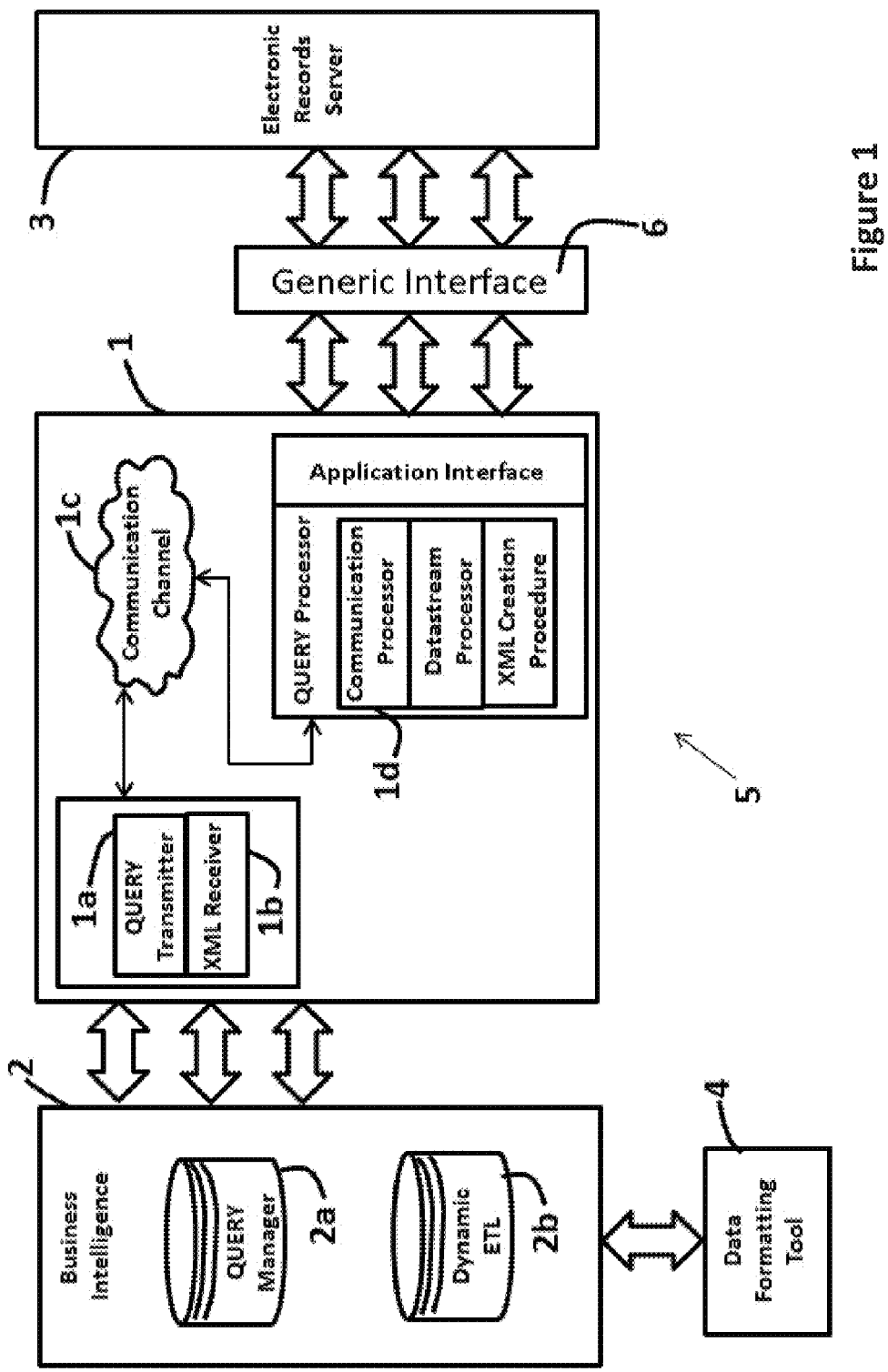
FIG. 1 is a schematic representation of a dynamic data management system constructed according to the teachings of the present disclosure.

The following description is merely exemplary in nature and is in no way intended to limit the present disclosure or its application or uses. For example, a data management system made and used according to the teachings contained herein is described throughout the present disclosure in conjunction with an electronic medical or health record system (EMR/EHR) in order to more fully illustrate the system and method of use. The incorporation and use of such a data management system in conjunction with other information storage systems, including but not limited to Advanced Health Care Registry and Immunization Registry, is contemplated to be within the scope of the disclosure. It should be understood that throughout the description and drawings, corresponding reference numerals indicate like or corresponding parts and features.

The present disclosure generally, provides a dynamic system and a method of using said system that provides a secure, real-time method of locating and extracting patient information stored as part of a health care directive registry or over a more disperse network, such as a health information exchange (HIE), followed by dimensional modeling said information and reporting the same. This dynamic system provides the ability to have the application residing at a remote site that can query and retrieve information in response to the query or multiple queries from multiple databases. The type of information that is sought may include, but not be limited to medical and legal documents submitted by individuals or on behalf of individuals and stored in electronic format in one or more databases located at or managed by hospitals, medical providers, insurance agencies, medical organizations, clinics, and the Department of Health, among others. Examples of such documents include Health Care Power of Attorney, Advance Directive, Declaration of Anatomical Gift, and other medical documents.

The data management system includes a request or order for information about an individual or group of individuals, wherein such information may reside as an electronic record (e.g., EMR/EHR) on a server managed by an organization as part of a health care directive registry or the like. The server may be linked to a document management and storage system (DMSS) and an advanced data collection and conversion system (DCCS), such as that commercially available as D3™ (Unival Inc., Ann Arbor, Mich.). The DMSS may include software designed to manage and control the storage of electronic documents through the application processor. One example of such software, among others, is commercially available as ProData™ (Unival Inc., Ann Arbor, Mich.). The DCCS includes at least one or more other servers that are in communication with EMR/EHR server and the DMMS. The DCCS can communicate with handheld devices or other types of mobile devices to quickly and accurately extract data from paper or electronic records, data warehouses, and other data streams or stores.

The DCCS is preferably a multiple-application system such that it can, when desirable, simultaneously produce comprehensive, customized web-based reports for every data collection request. The DCCS can collect the data at the point-of-care, from remote locations, or from electronic documents directly uploaded into the DCCS. The DCCS preferably works with industry standard formats, such as continuity of care documents (CCD), continuity of care records (CCR), or health level seven (HL7)Messaging, among others to allow for interoperability with any standard electronic health record system.

A further description of the DMSS and DCCS included as part of data management system in the current disclosure is provided in U.S. Pat. No. 7,519,622 issued to R. Fernandez on Apr. 14, 2009 and U.S. patent application Ser. No. 13/025,250 filed on Feb. 11, 2011, the entire contents of which are hereby incorporated by reference.

Referring to FIG. 1, the data management system 5 generally comprises an electronic records server 3. An interface application program running as part of the DCCS 1 links a query processor to a generic interface 6 that is in communication with the sources information on the server 3. This interface application through the generic interface 6 searches through the source information stored on a server 3 to extract data in accordance with directions in an associated tool set and data set.

Still referring to FIG. 1, the DCCS 1 stores in a Query manager 2a of a business intelligence engine 2, all queries connected to the electronic records server 3. The DCCS 1 transports medical records from the source system 3 and creates some form of XML 1d document taking the form of a Continuity of Care Record (CCR) or Continuity of Care Document (CCD). The XML document 1d is transmitted to the business intelligence engine 2 via a communication channel 1c through a query transmitter 1a working in conjunction with an XML receiver 1b. This begins a defined process undertaken by the business intelligence engine 2 of extracting, transforming, and loading a dynamic ETL system 2b The dynamic ETL system 2b populates a database table that contains the XML data source and could contain other information regarding the source information or other identifiable information such as provider, location, patient identifier to name a few examples. The XML field may contain medical record information for a patient such as medication, problems, procedures, immunizations, and encounters, among others. This information could then be used as virtual tables by methodology defined in the database application to breakdown the XML information. These virtual tables could for example, create information that would begin to define a group of de-normalized fact tables. These de-normalized fact tables may comprise the atomic data elements that can be identified as the core elements of the medical record. Any other information necessary or desirable for analytical reporting can be located in dimensional tables in existences or created herein. These dimensional tables may describe the elements of the atomic elements and together with the de-normalized fact tables establish a dimensional cube that may be used as a data formatting tool 4 for analytical reporting.

One unique aspect of the data management system of this disclosure is that the data that becomes a part of the previously described dimensional cube is dynamic. In other words, the medical or health records are ever changing and the elements of the XML are updated based on a configurable update of information at predetermined time intervals or upon predetermined events.

In addition to dimensional modeling analytical reporting there is also another form of reporting that uses the same data to create detailed and filtered reports which can include aggregate information for a user, e.g., all patients that would have had some medication or a diabetic condition, among other examples. This other form of reporting will not require as much processing to create a detailed report, but can be used in a predetermined manner, including but not limited to managing the office procedures that ensure care is given to patients that might not have an appointment in a given period of time, but require treatment of a condition, such as diabetes.

According to another aspect of the present disclosure, a method of using the aforementioned data management system to obtain, analyze, and report desired patient information in real-time is provided. This method 100, as shown in FIG. 2, generally comprises the steps of providing an order 105 in the form of a query that requests information regarding a specific patient or group of patients; providing an electronics records server 110 upon which the information regarding the specific patient or group of patients resides as source information; providing a data collection and conversion system (DCCS) 115; providing a business intelligence engine 120 that is in communication with the DCCS; causing the DCCS to transport 125 the information from the electronic records server and to create a document that includes XML data; causing the business intelligence engine to analyze or break down 130 the XML data to form at least one de-normalized fact table containing the desired patient information; and using 135 the de-normalized fact table to report the desired information in real-time. In performing this method 100, the DCCS comprises a query processor and an application interface capable of linking the query processor with the electronic records server through a generic interface.

The business intelligence engine used in this method 100 may include a dynamic ETL system and a query manager that is capable of interacting 140 with the DCCS. The business intelligence engine may be used to further form 145 at least one dimensional table in addition to the at least one de-normalized table. The de-normalized and dimensional tables defining 150 a dimensional cube for use as a data formatting tool in reporting. The dimensional cube may be dynamically updated 155 at predetermined time intervals or upon predetermined events.

The foregoing description of various embodiments of the present disclosure has been presented for purposes of illustration and description. It is not intended to be exhaustive or to limit the present disclosure to the precise embodiments disclosed. Numerous modifications or variations are possible in light of the above teachings. The embodiments discussed were chosen and described to provide the best illustration of the principles included in the present disclosure and its practical application to thereby enable one of ordinary skill in the art to utilize the teachings of the present disclosure in various embodiments and with various modifications as are suited to the particular use contemplated. All such modifications and variations are within the scope of the present disclosure as determined by the appended claims when interpreted in accordance with the breadth to which they are fairly, legally, and equitably entitled.

What is claimed is:

1. A dynamic data management system for locating, obtaining, analyzing, and reporting desired patient information in real-time, the system comprising:
    an order in the form of a query that requests information regarding a specific patient or group of patients that resides as source information in at least one location within multiple distributed data sources; the at least one location within the multiple data sources identified as being on an electronics records server; and
    at least one hardware processor including:
        memory;
        a document management and storage system (DMSS) having an application processor and a tool processor that manages and controls the storage of electronic documents through the use of an application program;
        the application program including functionality that selects a tool and authenticates the order; and
        at least one tool to send the query to the electronics records server and retrieving the source information; the at least one tool utilizing appropriate code to access the source information stored in the at least one location within the multiple distributed data sources via an interface application when an appropriate request is received; wherein the interface application continuously monitors and extracts in real-time the fact that a test has been ordered at the same time the source information is entered into the at least one location within the multiple distributed data sources; and
        a communication channel that allows communication between the application processor and the tool processor; and
        a data collection and conversion system (DCCS); the DCCS comprising:
            a query processor; and
            an application interface capable of linking the query processor with the electronic records server through a generic interface; and
        a business intelligence engine; the business intelligence engine being in communication with the DCCS;
        wherein the DCCS is capable of transporting the information from the electronic records server and creating a document that includes extensible markup language (XML) data; the business intelligence engine capable of breaking down the XML data to form at least one de-normalized fact table used to report the desired information in real-time from the at least one location in the multiple distributed data sources.

2. The data management system of claim 1, wherein the DCCS further comprises:
    a communication channel;
    a query transmitter; and
    an extensible markup language (XML) receiver.

3. The data management system of claim 1, wherein the business intelligence engine comprises:
    a query manager capable of interacting with the DCCS; and
    a dynamic extracting, transforming, & loading (ETL) system.

4. The data management system of claim 3, wherein the dynamic ETL system includes the de-normalized fact tables and dimensional tables.

5. The data management system of claim 4, wherein the de-normalized tables and dimensional tables define a dimensional cube that is used as a data formatting tool for reporting.

6. The data management system of claim 5, wherein the dimensional cube is dynamically updated at predetermined time intervals or upon predetermined events.

7. The data management system of claim 1, the system further comprising a document management and storage system (DMSS) having an application processor and a tool processor designed to manage and control the storage of electronic documents.

8. The data management system of claim 1, wherein the query processor further comprises a communication processor; a datastream processor, and an extensible markup language (XML) creation procedure system.

9. The data management system of claim 1, wherein the electronic records server contains one selected from the group of electronic medical records (EMR) and electronic health records (EHR).

10. A method of locating, obtaining, analyzing, and reporting desired patient information in real-time, the method comprising the steps of:

storing information via the at least one hardware processor regarding a specific patient or group of patients as source information in at least one location within multiple data sources residing on an electronics records server;

receiving by at least one hardware processor, an order in the form of a query that requests information regarding the specific patient or group of patients;

managing and controlling via the at least one hardware processor the storage of electronic documents through the use of an application program located on a document management and storage system (DMSS) having an application processor and a tool processor; wherein the application program selects at least one tool and authenticates the order;

sending the query via the at least one hardware Processor to the electronics records server and retrieving the source information using an interface application with at least one tool that includes appropriate code to access the source information stored in the at least one location within the multiple data sources when an appropriate request is received;

continuously monitoring and extracting in real-time using the interface application in the at least one hardware processor the fact that a test has been ordered at the same time the information is entered as source information into the at least one location within multiple data sources;

linking in the at least one hardware processor a query processor in a data collection and conversion system (DCCS) with the electronics records server through the use of a generic interface established by an application interface in the DCCS;

allowing the at least one hardware processor via a business intelligence engine to communicate with the DCCS;

transporting by the DCCS in the at least one hardware processor the source information from the electronic records server;

creating a document by the DCCS in the at least one hardware processor that includes extensible markup language (XML) data;

breaking down the XML data by the business intelligence engine in the at least one hardware processor to form at least one de-normalized fact table containing the desired patient information; and using the de-normalized fact table by the at least one hardware processor to report the desired information in real-time from the location in the multiple distributed data sources.

11. The method of claim 10, wherein communicating between the business intelligence engine and the DCCS in the at least one hardware processor includes the business intelligence engine having a query manager capable of interacting with the DCCS and a dynamic extracting, transforming, & loading (ETL) system.

12. The method of claim 11, wherein the method further includes forming through the business intelligence engine in the at least one hardware processor at least one dimensional table in addition to the at least one de-normalized table.

13. The method of claim 12, wherein the method further includes defining a dimensional cube in the at least one hardware processor for use as a data formatting tool in reporting; the dimensional cube including the de-normalized and dimensional tables.

14. The method of claim 13, wherein the method further includes dynamically updating in the at least one hardware processor the dimensional cube at predetermined time intervals or upon predetermined events.

* * * * *